United States Patent
Derose et al.

(10) Patent No.: US 6,812,010 B1
(45) Date of Patent: Nov. 2, 2004

(54) METHOD FOR ENZYMATIC PREPARATION OF HOMOGENTISATE

(75) Inventors: Richard Derose, Evry (FR); Alain Sailland, Lyons (FR)

(73) Assignee: Aventis Cropscience SA (FR)

( * ) Notice: Subject to any disclaimer, the term of this patent is extended or adjusted under 35 U.S.C. 154(b) by 0 days.

(21) Appl. No.: 09/582,482

(22) PCT Filed: Dec. 22, 1998

(86) PCT No.: PCT/FR98/02819

§ 371 (c)(1),
(2), (4) Date: Oct. 13, 2000

(87) PCT Pub. No.: WO99/34008

PCT Pub. Date: Jul. 8, 1999

(30) Foreign Application Priority Data

Dec. 24, 1997 (FR) .............................. 97 16727

(51) Int. Cl.[7] .............................. C12P 7/40; C12P 7/42
(52) U.S. Cl. .................. 435/136; 435/146; 435/440; 435/453; 435/410; 435/276; 435/277; 435/278
(58) Field of Search .................. 435/136, 146, 435/440, 453, 410, 276, 277, 278

(56) References Cited

PUBLICATIONS

Blakley et al., Canadian Journal of Microbiology, vol. 23, 1977, pp. 1128–1139.*
Suemori et al., Journal of Fermentation and Bioengineering, vol. 81, No. 2, 1996, pp. 133–137.*
Hareland et al., J. of Bacteriology, vol. 121, No. 1, 1975, pp. 272–285.*
Suemori et al., Semei Kogaku Kogyo Gijustsu Kenkyusho Kenkyu Hokoku (1995), 3(2), 33–36.*

* cited by examiner

*Primary Examiner*—Irene Marx
(74) *Attorney, Agent, or Firm*—Connolly Bove Lodge & Hutz LLP

(57) ABSTRACT

The invention concerns a method for enzymatic preparation of homogentisate (HMO) from 4-hydroxypyruvate (HPP), characterized in that it consists in carrying out in a suitable reaction medium the following enzymatic reactions: enzymatic conversion of HPP into 4-hydroxyphenylacetate (HPA) with a first appropriate enzyme; then an enzymatic conversion of HPA into HMO with a second appropriate enzyme.

8 Claims, No Drawings

METHOD FOR ENZYMATIC PREPARATION OF HOMOGENTISATE

The present invention relates to a novel method for enzymatic preparation of homogentisate, or 2,5-dihydroxyphenylacetic acid (hereafter HMO).

HMO is a known precursor of molecules termed ochronotic pigments which are melanin analogues. These brown molecules are, moreover, often cited as "melanin-like pigments" which find a varied application in cosmetics or the pharmaceutical industry. The addition of melanin or melanin-like pigments to antisun milks would have an advantageous protective effect. To produce these ochronotic derivatives from HGA, the method is simple since the molecule self-oxidizes rapidly under alkaline conditions. Various methods for enzymatic preparation of HMO from 1-phenylacetic acid or from tyrosine are described in the prior art (WO 93/08295 or EP 343 330), as well as the subsequent preparation of melanin.

It is also known that HMO is a compound which is essential to plant life. In plant cells, HMO is the product of enzymatic transformation of 4-hydroxyphenylpyruvate (hereafter HPP) with 4-hydroxyphenylpyruvate dioxygenase (hereafter HPPD). Inhibitors of this enzyme are herbicidal compounds which block the production of HMO in plant cells (Pallett K. E. et al. 1997 *Pestic. Sci.* 50 83–84). When plants of *Arabidopsis thaliana* for example, are germinated on synthetic medium in the presence of an HPPD inhibitor, the plants will germinate, remain white and then die very rapidly. However, if HMO is added to the synthetic medium supplemented with an HPPD inhibitor, the plants will germinate normally and remain green as long as the medium contains HMO. It is thus also important to have HMO available to prevent deficiencies in plants which are linked to a natural or induced, in particular by HPPD inhibitors, metabolic dysfunction of HMO biosynthesis.

The present invention thus relates to a method for enzymatic preparation of HMO from HPP, and more particularly to a method for enzymatic preparation of HMO from HPPD-inhibitor-insensitive HPP.

The method according to the invention consists in carrying out, in a suitable reaction medium, the following enzymatic reactions:

enzymatic conversion of HPP into 4-hydroxyphenylacetate (hereafter HPA) with a first suitable enzyme, then enzymatic conversion of HPA into HMO with a second suitable enzyme.

The following first enzymatic reaction

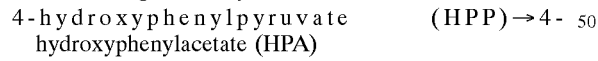

is catalysed by a suitable HPP-oxidase. Such oxidases are found in many prokaryotic or eukaryotic species, in particular in bacteria which can grow on HPP as the only carbon source, transforming it into HPA, more particularly in an *Arthrobacter* in which such an oxidase is responsible for a step in tyrosine catabolism (Blakley, E. R. 1977 *Canadian Journal of Microbiology* 23 1128–1139).

The following second enzymatic reaction:

4-hydroxyphenylacetate (HPA)→homogentisate (HMO) is catalysed by a suitable HPA-hydroxylase. Such hydroxylases are found in many prokaryotic or eukaryotic species, in particular in bacteria which can grow on HPA as the only carbon source, transforming it into HMO, more particularly in *Pseudomonas acidovorans*, often termed *Comamonas acidovorans* (Hareland, W. A. et al 1975 *Journal of Bacteriology* 121 272–285), in certain *Xanthobacter* (Van Den Tweel W. J. J. et al. 1986 *Antonie val Leeuwenhoek* 52 309–318), in *Pseudomonas alcaligenes* (Karigar C. S. and Pujar B. G. 1993 *FEMS Microbiology Letters* 110 59–64), in *Flavobacterium* sp. (Van Den Tweel W. J. J. et al. 1988 *Arch Microbiol.* 149 207–213), in *Bacillus subtillis* (Crawford R. L. 1978 *FEMS Microbiology Letters* 4 233–234), in *Nocardia* sp. DM1 (Raju S. G. and Vaidyanathan C. S. 1986 *J. Indian Inst. Sci.* 66 511–520) and in *Rhodococcus erythropolis* (Suemori A. et al. 1996 *Journal of Fermentation And Bioengineering* Vol. 81, No. 2 133–137).

The HPA-hydroxylase used in the method according to the invention is advantageously extracted from *Pseudomonas acidovorans*.

According to a preferential embodiment of the invention, both enzymatic reactions are carried out in the same reaction medium containing HPP, the two suitable enzymes being present together at the same time in the reaction medium.

The two suitable enzymes can be introduced into the suitable reaction medium in the form of protein extract, said protein extract being able to be crude or totally or partially purified, or alternatively they can be produced in situ by suitable biological organisms. They can thus be produced in situ by each biological organism which naturally produces the two enzymes, or alternatively by a single biological organism which has been modified so as to produce the two enzymes. This biological organism can be a bacterium, a yeast or a plant cell.

Since the two enzymes are insensitive to HPPD inhibitors, the method according to the invention can be performed in the presence of an HPPD inhibitor in the suitable reaction medium.

The suitable reaction medium consists of any aqueous medium in which the temperature, pH and ionic strength conditions are suitable for the enzymatic reactions. When the enzymes are produced in situ by one or more biological organisms, the reaction medium is suitable for the growth of said organisms.

At the end of the reaction, HMO can be isolated from the reaction medium and purified, or left in the reaction medium. In this second case, the reaction medium containing HMO can be used as a nutrient medium for culturing plants, more particularly for culturing plants which exhibit a natural or induced, in particular by HPPD inhibitors, metabolic dysfunction of HMO biosynthesis.

The examples below make it possible to illustrate the invention, without however seeking to limit the scope thereof.

EXAMPLE 1

Production of HPA from HPP Using a Protein Extract from *Arthrobacter*

*Arthrobacter* Culture:

*Arthrobacter globiformis* is cultured at 28° C. and 220 rpm for 20 hours in a 250-ml Erlenmeyer flask containing 50 ml of medium A supplemented with 0.1% L-tyrosine and 0.01% of yeast extract [medium A composed, in grams per liter, of $KH_2PO_4$ (1.5) $K_2HPO_4.3H_2O$ (3.5) $NH_4NO_3$ (1) $FeSO_4.7H_2O$ (0.1) $ZnSO_4.7H_2O$ (0.01) $NaMoO_2.7H_2O$ (0.01) $CaCl_2.2H_2O$ (0.01) $MgSO_4.7H_2O$ (0.05)].

Extraction and Assay of HPP-Oxidase Activity

A cell pellet is recovered from 2.1 liters of culture by centrifugation at 3000×g for 15 min. The pellet is washed with distilled water and then recentrifuged. All subsequent steps are carried out at 4° C.

The cell pellet, which is approximately 3.4 g, is resuspended in 7 ml of extraction buffer (0.05 M potassium phosphate pH 7.5, 0.1 mM TPP, 0.1 mM $MgCl_2$ and 5 mM mercaptoethanol) and sonicated twice at 23 kHz for 2.5 min. The resulting suspension is centrifuged at 44,000×g for 20 min. The harvested supernatant is again centrifuged at 100,000×g for 60 min. 0.7 ml of 2% protamine sulphate in the extraction buffer is added to the new 7-ml supernatant, followed by gentle stirring. The precipitate which forms is removed by a centrifugation at 20,000×g for 20 min. Ammonium sulphate is gradually added to the supernatant thus obtained so as to reach 60% saturation. This new preparation is stirred for 30 min., and the precipitate formed harvested by centrifugation at 20,000×g for 20 min. The pellet is redissolved in 0.5 ml of extraction buffer and aliquoted in 0.1-ml fractions, these fractions being kept at −80° C. before use.

The HPP-oxidase activity is measured in a 96-well microtitration plate with 200 μl of reaction per well consisting of 149.8 μl of 67 mM sodium phosphate pH 7.4, 10 μl of 13.4 mM glutathione, 10 μl of 67 mM MgCl2, 10 μl of 26.7 mM TPP, 10 μl of 67 μM FAD, 0.2 μl of protein (i.e. approximately 6 μg) and 10 μl of 2.5 mM HPP.

When an assay for inhibition by an HPPD inhibitor is carried out, 2 μl of 10 mM 4-[4-trifluoromethyl-2-(methylsulphonyl)benzoyl]-5-cyclopropylisoxazole are added to a phosphate buffer containing 20% of DMSO.

The reaction is initiated by adding the substrate, HPP; it takes place at 30° C. for 5 min. with stirring. The reaction is stopped by adding 33 μl of 25% perchloric acid.

The plate is then centrifuged at 2000 rpm for 15 min., and the supernatant is analysed by HPLC. 50 μl of the supernatant is injected onto a Spherisorb ODS2 column equilibrated with buffer A (5.5% acetonitrile, 0.1% TFA) at the flow rate of 1.5 ml/min.

The elution programme used is:
0 min.: 0% of buffer B (acetonitrile)
6 min.: 15% of buffer B
6.5 min.: 15% of buffer B
7 min.: 60% of buffer B
8 min.: 60% of buffer B
8.5 min.: 0% of buffer B The detection is carried out at 276 nm.

The HPA produced by the enzymatic extract from HPP is compared with a reference consisting of commercial HPA, in terms of retention time and spectral absorption peak.

Results

The HPLC analysis shows that the protein extract extracted from Arthrobacter globiformis cultured on tyrosine as the major carbon source is capable of transforming the HPP into HPA (the molecule produced comigrates perfectly with the commercial reference HPA).

The enzyme responsible for this reaction is not inhibited by 100 μM of HPPD inhibitor.

EXAMPLE 2

Production of HMO from HPA Using a Protein Extract from *Pseudomonas*

Organism Culture

*Pseudomonas acidovorans* is cultured at 28° C. and 220 rpm for 20 hours in a 250-ml Erlenmeyer flask containing 50 ml of medium B supplemented with 0.15% HPA and 0.01% of nitrilotriacetic acid [medium B composed, in grams per liter, of $NaH_2PO_4$ (1) $K_2HPO_4.3H_2O$ (4.25) $NH_4Cl$ (2) $FeSO_4.7H_2O$ (0.012) $ZnSO_4.7H_2O$ (0.003) $MnSO_4.7H_2O$ (0.003) $CoSO_4.7H_2O$ (0.01) $MgSO_4.7H_2O$ (0.2)].

Extraction and Assay of HPA-Hydroxylase Activity

A cell pellet is recovered from 0.1 liter of culture by centrifugation at 7500×g for 10 min. The pellet is washed with distilled water and then recentrifuged. All subsequent steps are carried out at 4° C.

The cell pellet, which is approximately 0.5 g, is resuspended in 1.5 ml of extraction buffer (0.1 M potassium phosphate pH 7.2, 1 mM DTE and 5 mM $MgMgSO_4$) and sonicated twice at 23 kHz for 2.5 min. The resulting suspension is centrifuged at 44,000×g for 20 min. The harvested supernatant is again centrifuged at 100,000×g for 60 min. The new supernatant is aliquoted in 0.1-ml fractions, these fractions being kept at −80° C. before use.

The HPA-hydroxylase activity is measured in a 96-well microtitration plate with 200 μl of reaction per well consisting of 150 μl of 0.1 M sodium phosphate fits pH 7.2, 10 μl of 20 mM DTE, 10 μl of 3 mM NADH, 15 μl of 67 μM FAD, 10 μl of protein (i.e. approximately 7 μg) and 5 μl of 10 mM HPA.

When an assay for inhibition by an HPPD inhibitor is carried out, 2 μl of 10 mM 4-[4-trifluoromethyl-2-(methylsulphonyl)benzoyl]-5-cyclopropylisoxazole are added to a phosphate buffer containing 20% of DMSO.

The reaction is initiated by adding the substrate, HPA; it takes place at 30° C. for 5 min. with stirring. The reaction is stopped by adding 33 μl of 25% perchloric acid.

The plate is then centrifuged at 2000 rpm for 15 min., and the supernatant is analysed by HPLC. 10 μl of the supernatant is injected onto a Spherisorb ODS2 column equilibrated with buffer A (5.5% acetonitrile, 0.1% TFA) at the flow rate of 1.5 ml/min.

The elution programme used is:
0 min.: 0% of buffer B (acetonitrile)
0.8 min.: 0% of buffer B
1 min.: 60% of buffer B
1.7 min.: 60% of buffer B
1.9 min.: 0% of buffer B
5 min.: 0% of buffer B The detection is carried out at 292 nm.

The HMO produced by the enzymatic extract from HPA is compared with a reference consisting of commercial HMO, in terms of retention time and spectral absorption peak.

Results

The HPLC analysis made it possible to show that the protein extract extracted from *Pseudomonas acidovorans* is capable of transforming the HPA into HMO (the molecule produced comigrates perfectly with the commercial reference HMO).

The enzyme responsible for this reaction is not inhibited under our assay conditions by 100 μM of HPPD inhibitor.

EXAMPLE 3

Production of HMO from HPP using a Protein Extract From *Arthrobacter* and From *Pseudomonas*

HPA-Hydroxylase Activity-Coupled HPP-Oxidase Activity

The HPA-hydroxylase activity-coupled HPP-oxidase activity is measured in a 96-well microtitration plate with 200 μl of reaction per well consisting of 100 μl of 100 mM sodium phosphate pH 7.2, 10 μl of 20 mM DTE, 10 μl of 3 mM NADH, 15 μl of 67 μM FAD, 10 μl of 13.4 mM glutatione, 10 μl of 67 mM MgCl2, 10 μl of 26.7 mM TPP, 2 μl of HPP-oxidase extract (i.e. approximately 60 μg), 25 μl of HPA-hydroxylase extract (i.e. approximately 18 μg) and 10 μl of 10 mM HPP.

The reaction is initiated by adding the substrate, HPP; it takes place at 30° C. for 30 min. with stirring. The reaction is stopped by adding 33 µl of 25% perchloric acid.

The plate is then centrifuged at 2000 rpm for 15 min., and the supernatant is analysed by HPLC. 25 µl of the supernatant is injected onto a Spherisorb ODS2 column equilibrated with buffer A (5.5% acetonitrile, 0.1% TFA) at the flow rate of 1.5 ml/min.

The elution programme used is:
0 min.: 0% of buffer B (acetonitrile)
6 min.: 15% of buffer B
6.5 min.: 15% of buffer B
7 min.: 60% of buffer B
8 min.: 60% of buffer B
8.5 min.: 0% of buffer B The detection is carried out at 276 nm and 292 nm simultaneously.

Results

The HPLC analysis made it possible to show that the protein extract extracted from *Arthrobacter globiformis* combined with that from *Pseudomonas acidovorans* is capable of simultaneously transforming HPP into HMO (the molecule produced comigrates perfectly with the commercial reference HMO).

What is claimed is:

1. A method for enzymatic preparation of homogentisate (HMO) from 4-hydroxyphenylpyruvate (HPP), wherein said method consists in carrying out, in a suitable reaction medium, the following enzymatic reactions:

enzymatic conversion of HPP into 4-hydroxyphenylacetate (HPA) with an amount of a first suitable enzyme effective to convert HPP into HPA, wherein said first suitable enzyme is a suitable HPP-oxidase, then enzymatic conversion of HPA into HMO with an amount of a second suitable enzyme effective to convert HPA into HMO, wherein said second suitable enzyme is a suitable HPA-hydroxylase, wherein said enzymatic reactions are carried out in the presence of a 4-hydroxyphenylpyruvate dioxygenase (HPPD) inhibitor in said suitable reaction medium, wherein said HPPD inhibitor is present in said suitable reaction medium in an amount that does not inhibit the enzymatic activity of said first suitable enzyme or said second suitable enzyme.

2. The method according to claim 1, wherein the HPP-oxidase originates from bacteria which grow on HPP as the only carbon source.

3. The method according to claim 1, wherein the HPP-oxidase originates from Arthrobacter.

4. The method according to claim 1, wherein the HPA-hydroxylase originates from bacteria which grow on HPA as the only carbon source.

5. The method according to claim 4, wherein the bacteria are selected from the group consisting of *Pseudomonas acidovarans, Xanthobacter, Pseudomonas alcaligenes, Flavobacterium* sp., *Bacillus subtillis*, and *Rhodococcus erythropolis*.

6. The method according to claim 1, wherein the HPA-hydroxylase is extracted from *Pseudomonas acidovarans*.

7. The method according to claim 1, wherein both enzymatic reactions are carried out in the same reaction medium containing HPP, the two suitable enzymes being present together at the same time in the reaction medium.

8. The method according to claim 1, wherein the two suitable enzymes are introduced into suitable reaction medium in the form of protein extracts from bacteria, yeast or plant cells, or alternatively they are produced in situ by suitable bacteria, yeast or plant cells.

* * * * *